United States Patent
Kon et al.

(10) Patent No.: US 6,401,522 B1
(45) Date of Patent: Jun. 11, 2002

(54) GAS ANALYZER AND METHOD OF CALIBRATING THE SAME

(75) Inventors: Masao Kon, Nagoya; Takao Murase, Konan, both of (JP)

(73) Assignee: NGK Insulators, Ltd. (JP)

( * ) Notice: Subject to any disclaimer, the term of this patent is extended or adjusted under 35 U.S.C. 154(b) by 0 days.

(21) Appl. No.: 09/664,522

(22) Filed: Sep. 18, 2000

(30) Foreign Application Priority Data

Sep. 22, 1999 (JP) .......................................... 11-268410

(51) Int. Cl.⁷ ........................... G01N 27/41; G01N 7/00
(52) U.S. Cl. ...................... 73/31.05; 204/424; 204/425; 204/426; 204/427
(58) Field of Search ................................ 73/1.03, 1.06, 73/23.21, 23.31, 23.32, 31.05; 204/424, 425, 426, 427, 428, 429

(56) References Cited

U.S. PATENT DOCUMENTS

| | | | |
|---|---|---|---|
| 5,413,683 A | * 5/1995 | Murase et al. | 204/425 |
| 5,672,811 A | * 9/1997 | Kato et al. | 73/31.05 |
| 5,778,866 A | * 7/1998 | Uchikawa | 73/1.06 |
| 5,780,710 A | 7/1998 | Murase et al. | |
| 6,254,750 B1 | * 7/2001 | Patrick et al. | 204/425 |
| 6,290,840 B1 | * 9/2001 | Kato et al. | 205/784.5 |
| 6,319,377 B1 | * 11/2001 | Hasei et al. | 204/425 |

FOREIGN PATENT DOCUMENTS

| | | |
|---|---|---|
| DE | 198 52 247 A1 | 6/1999 |
| DE | 198 03 805 A1 | 8/1999 |
| EP | 0 678 740 A1 | 10/1995 |
| EP | 0 769 693 A1 | 4/1997 |
| EP | 0 810 433 A2 | 12/1997 |
| JP | 63-38154 | 2/1988 |
| JP | 64-39545 | 2/1989 |
| JP | 1-277751 | 11/1989 |
| JP | 2-1543 | 1/1990 |
| JP | 8-271476 | 10/1996 |
| JP | 9-113484 | 5/1997 |
| JP | 10-73563 | 3/1998 |

* cited by examiner

Primary Examiner—Hezron Williams
Assistant Examiner—Michael Cygan
(74) Attorney, Agent, or Firm—Parkhurst & Wendel, L.L.P.

(57) ABSTRACT

A gas analyzer monitors concentration of discharged NOx even if an air ratio X is less than 1. The gas analyzer has three internal spaces and four electro-chemical pumps. The first space effects combustion of combustible gases and has a first pump to adjust oxygen partial pressure. The second space has a second pump to decrease oxygen partial pressure. The third space has a third electro-chemical pump to control oxygen partial pressure and a fourth pump to draw out oxygen generated when object gas is reduced or decomposed. An air introducing duct is provided so the outside pump electrodes of the first and second pumps are isolated and not directly exposed to object gas. This duct serves as oxygen source when oxygen is introduced into the first space. The gas analyzer has an operating section for operating the pumps, a calculating section, and a displaying/outputting section. A calibrating method is disclosed also.

9 Claims, 8 Drawing Sheets

GAS ANALYZER AND METHOD OF CALIBRATING THE SAME

BACKGROUND OF THE INVENTION

1. Field of the Invention

The present invention relates to a gas analyzer for measuring a gas (hereinafter referred to as object gas) containing a certain component (hereinafter referred to as object component) such as $NO_x$ including a combined oxygen, and a method for calibrating the gas analyzer.

2. Description of the Related Art

In the past, various methods and apparatus had been suggested which were used to measure the concentration of an object component contained in an object gas. For example, as a method for measuring $NO_x$ contained in an object gas such as a combustible gas, there has been known a process which involves the use of a gas sensor manufactured by forming Pt electrode and Rh electrode on an oxygen ion conductive solid electrolytic material such as zirconia, and which achieves the desired measurement by making use of a reducibility which Ph can provide for reducing $NO_x$ and by generating an electro motive force between two electrodes. However, such a gas sensor has been found to have the following disadvantages. Namely, if an oxygen concentration of an object gas (which might be a combustible gas) varies, such a variation will cause not only a significant change in the electro motive force, but also a trouble that the electromotive force will change only very slightly with respect to a change in $NO_x$ concentration. As a result, it is difficult to complete the desired measurement without being influenced by the above troubles.

Another disadvantage associated with the above mentioned prior art may be concluded as follows. Namely, in order to reduce the $NO_x$ component, a reductive gas such as CO is indispensable. However, under a condition where a large amount of $NO_x$ is generated and hence the fuel amount becomes extremely small, an amount of CO generated will become less than an amount of $NO_x$ generated. As a result, using a combustible gas formed under such a combustion condition has been found unable to perform the desired measurement.

Further, JP-A-63-38154 and 64-39545 have proposed that a series of electrochemical pump cells and sensor cells formed by Pt electrode and an oxygen ion conductive solid electrolytic material can be combined with another series of electro-chemical pump cells and sensor cells formed by Rh electrode and an oxygen ion conductive solid electrolytic material, so that $NO_x$ concentration may be measured by making use of differences between the electric current values of various pump cells.

Moreover, JP-A-1-277751 and JP-A-2-1543 have proposed a method comprising the steps of preparing a pair of electro-chemical pump cells and a pair of sensor cells, measuring a critical pump current under an oxygen partial pressure wherein $NO_x$ is not reduced with a sensor comprising one set out of two sets of pairs of the chemical pump cells and the sensor cells, and measuring a critical pump current under an oxygen partial pressure wherein $NO_x$ is reduced with another sensor which is the other pair of the pump cell and the sensor cell, then calculating a difference between the two critical pump currents; or employing a sensor comprising a pair of a pump cell and a sensor cell, and measuring a difference in the critical current by measuring a critical current by changing an oxygen partial pressure of an object gas between the cases wherein $NO_x$ is not reduced and wherein $NO_x$ is reduced.

However, when using the above described method for measuring $NO_x$, most amount of a critical current value is occupied by an electric current generated by virtue of a large amount of oxygen contained in an object gas. Since an electric current value based on an object component $NO_x$ becomes extremely small, a difference between two large current values can be used to calculate only a small current value corresponding to the concentration of the object component $NO_x$. For this reason, there has been a problem that when a change-over is conducted between one pair of sensors, it is impossible to perform a continuous measurement, or the measurement has only a decreased responsibility and a decreased precision. On the other hand, in the case of using two pairs of sensors, if an oxygen concentration of an object gas has a significant change, an error is likely to occur in a measured value. As a result, if an oxygen concentration of an object gas has a significant change, it is not allowed to use the above method disclosed in the above prior arts. This is because a dependency of a pump current on the oxygen concentration on one sensor will be different from a dependency of a pump current on the oxygen concentration on the other. In addition, when a difference occurs between two pairs of sensors with the elapse of time, such a difference will become an error, causing a problem that these sensors can not be used for a long time.

In view of the above, it has been made clear that an amount of oxygen existing in an object gas is responsible for a decreased measurement precision when measuring $NO_x$ or other object components.

In order to solve the problems described in the above, a further method has been proposed by JP-A-8-271476. According to this method, a first electro-chemical pump cell and a second electro-chemical pump cell are arranged in series so as to measure an object gas component (containing a combined oxygen) such as $NO_x$ contained in an object gas, and such a measurement can be performed continuously for a long time with a high responsibility, without having to be influenced by an oxygen concentration of the object gas. Further, according to this publication, an object gas containing an object component including a combined oxygen is introduced from an outside space into a first treatment zone under a predetermined diffusion resistance. Then, an amount of oxygen contained in an atmosphere within this zone is controlled in a first electro-chemical pump cell in the first treatment zone to a low partial pressure value which does not bring about any unfavourable influence to a measuring process to be carried out in a second treatment zone. On the other hand, in the second treatment zone, the object component contained in the atmosphere introduced from the first treatment zone is reduced or decomposed, an amount of oxygen generated at this moment is drawn out by virtue of an oxygen pumping action of a second electro-chemical pump cell. Subsequently, a pump current flowing into the second electro-chemical pump cell is detected which is then used to calculate an amount of object component contained in the object gas. However, even when using this improved method, there is still a problem, i.e., if the concentration of an oxygen contained in the object gas is high, such a high oxygen concentration will make it difficult to perform a correct measurement.

In order to solve the above problem, a still further method has been proposed by JP-A-9-113484 and JP-A-10-73563. According. to this method, a first electro-chemical pump cell, a second electro-chemical pump cell, and a third electro-chemical pump cell are arranged in series to measure an object gas component (containing a combined oxygen)

such as $NO_x$ contained in an object gas, and such a measurement can be performed continuously for a long time with a high responsibility, without having to be influenced by an oxygen concentration of the object gas. Further, according to these publications, an object gas containing an object component including a combined oxygen is introduced from an outside space into a first treatment zone and a second treatment zone successively under a predetermined diffusion resistance. Then, an oxygen partial pressure of an atmosphere within this zone is controlled in a first electrochemical pump cell in the first treatment zone to a low value which is sufficient to control the oxygen partial pressure in a second treatment zone. Subsequently, in the second treatment zone, the oxygen partial pressure of the atmosphere in the second treatment zone is controlled to a predetermined value by virtue of an oxygen pumping action effected by the second electro-chemical pump cell. Alternatively, in the first treatment zone, after the oxygen partial pressure of the atmosphere in the first treatment zone is controlled to a predetermined value by virtue of an oxygen pumping action effected by the first electro-chemical pump cell, the partial pressure is further controlled to a lower value which does not bring about any unfavorable influence to the measurement of the object component in the second treatment zone. Afterwards, in the third treatment zone, the object component of the atmosphere introduced from the second treatment zone is reduced or decomposed, an amount of oxygen generated at this moment is drawn out by virtue of an oxygen pumping action of a third electro-chemical pump cell. Therefore, a pump current flowing into the third electro-chemical pump cell may be detected which is then used to calculate an amount of object component contained in the object gas.

However, when using the sensors disclosed in the above two patent application publications, if an air ratio is $\lambda<1$, an electric current Ip3 corresponding to $NO_x$ concentration at this time will decrease as shown in FIG. 5. Further, it is understood that this phenomenon is particularly remarkable in a weak rich area where the air ratio $\lambda$ is close to 1. This is because when the air ratio is $\lambda \geq 1$, some coexisting combustible gases such as carbon monoxide, hydrocarbons and hydrogen gas will react with oxygen coexisting therein. In contrast, if the air ratio is $\lambda<1$, since an amount of the coexisting oxygen is not sufficient for the above combustion, the combustible gases will react with $NO_x$ which is an object gas component. As a result, the $NO_x$ component will disappear.

For this reason, the above described conventional methods and apparatus can not be used in the case where an object gas contains combustible gases such as carbon monoxide, hydrocarbons and hydrogen gas with a high concentration and where the air ratio is likely to become $\lambda<1$. Particularly, with regard to a gasoline engine in which the air ratio $\lambda$ varies in the vicinity of 1 and with regard to a lean-burn engine which produces periodic spikes, since it is impossible to avoid a situation in which the air ratio $\lambda$ is likely to become less than 1, there has not been an appropriate method capable of effectively monitoring a discharged $NO_x$.

SUMMARY OF THE INVENTION

Accordingly, it is an object of the present invention to provide an improved gas analyzer capable of correctly monitoring the concentration of a discharged $NO_x$ even if an air ratio $\lambda$ is less than 1. It is another object of the present invention to provide a gas analyzer calibrating method involving the use of the improved gas analyzer.

Namely, according to the present invention there is provided a gas analyzer comprising: a gas sensor which includes a first diffusion rate controlling passage, a first internal space communicated with the first diffusion rate controlling passage, a second diffusion rate controlling passage, a second internal space communicated with the second diffusion rate controlling passage, a third diffusion rate controlling passage, a third internal space communicated with the third diffusion rate controlling passage, and an air introducing duct; wherein the first diffusion rate controlling passage is a passage provided for introducing an object gas containing an object component including a sort of combined oxygen from an external gas existing space to the first internal space under a predetermined diffusion resistance; wherein the first internal space is provided for effecting the combustion of some combustible gases, and is provided with a first electro-chemical pump for adjusting an oxygen partial pressure within the first internal space, so that the internal space constantly contains a sufficient amount of oxygen capable of effecting the combustion of the combustible gases contained in the object gas which has been introduced into the internal space through the first diffusion rate controlling passage; wherein the second diffusion rate controlling passage is a passage provided for introducing the object gas treated in the first internal space to the second internal space under a predetermined diffusion resistance; wherein the second internal space is provided with a second electro-chemical pump which is so constructed that when an amount of oxygen is drawn from the second internal space atmosphere consisting of the object gas introduced into the second internal space through the second diffusion rate controlling passage, the oxygen partial pressure is decreased to a sufficiently low value which does not reduce or decompose the object gas and which is low enough for controlling the oxygen partial pressure in a third treatment zone; wherein the third diffusion rate controlling passage is a passage provided for introducing the object gas treated in the second internal space to the third internal space under a predetermined diffusion resistance; wherein the third internal space is provided with a third electro-chemical pump next to the third diffusion rage controlling passage and a fourth electro-chemical pump next to third electro-chemical pump, the third electro-chemical pump is so constructed that when the oxygen partial pressure of the atmosphere within the second internal space has a value which will not substantially reduce or decompose the object gas, the oxygen partial pressure is controlled to a further lower value which does not bring about any significant influence to the measurement of an amount of an object gas component, whereas the fourth electro-chemical pump is provided to reduce or decompose the object gas component introduced from the second internal space and to draw out an amount of oxygen generated at this moment; wherein the air introducing duct is provided in a manner such that the outside pump electrodes of the first and second electro-chemical pumps are isolated so that these electrodes are not directly exposed to the object gas and that this duct can serve as oxygen sources when oxygen is introduced into the first internal space; the gas analyzer further comprising: an operating section for operating the electro-chemical pumps provided in the first to third internal spaces of the gas sensor; a calculating section for performing a predetermined calculation on pumping currents flowing into the electro-chemical pumps so as to obtain a concentration value of the object gas component; a displaying/outputting section for displaying a value calculated in the calculating section or for outputting the value as an electric output; and a heater operating section for heating the gas sensor to a predetermined temperature.

Further, according to the present invention, a pumping current in the second treatment zone, a pumping current in the third treatment zone, and a pumping current in the fourth treatment zone are all introduced into the calculating section so as to receive a predetermined calculation, thereby making it possible to calculate and then output an oxygen concentration or an air/fuel ratio A/F or an air ratio λ. Here, the object gas component is $NO_x$ whose concentration may be calibrated in accordance with the calculated oxygen concentration or the air/fuel ratio A/F or the air ratio λ. Although it is preferred that at least the operating section and the amplifier are integrally formed with the gas sensor, such an operating section and an amplifier may also be separated from the gas sensor, but received into a receiver unit comprising a calculating section, displaying and outputting section, and heater operating section.

Moreover, according to the present invention, there is provided a gas analyzer calibrating method for use with a gas analyzer which comprises: a gas sensor which includes a first diffusion rate controlling passage, a first internal space communicated with the first diffusion rate controlling passage, a second diffusion rate controlling passage, a second internal space communicated with the second diffusion rate controlling passage, a third diffusion rate controlling passage, a third internal space communicated with the third diffusion rate controlling passage, and an air introducing duct; wherein the first diffusion rate controlling passage is a passage provided for introducing an object gas containing an object component including a sort of combined oxygen from an external gas existing space to the first internal space under a predetermined diffusion resistance; wherein the first internal space is provided for effecting the combustion of some combustible gases, and is provided with a first electro-chemical pump for adjusting an oxygen partial pressure within the first internal space, so that the internal space constantly contains a sufficient amount of oxygen capable of effecting the combustion of the combustible gases contained in the object gas which has been introduced into the internal space through the first diffusion rate controlling passage; wherein the second diffusion rate controlling passage is a passage provided for introducing the object gas treated in the first internal space to the second internal space under a predetermined diffusion resistance; wherein the second internal space is provided with a second electro-chemical pump which is so constructed that when an amount of oxygen is drawn from the second internal space atmosphere consisting of the object gas introduced into the second internal space through the second diffusion rate controlling passage, the oxygen partial pressure is decreased to a sufficiently low value which does not reduce or decompose the object gas and which is low enough for controlling the oxygen partial pressure in a third treatment zone; wherein the third diffusion rate controlling passage is a passage provided for introducing the object gas treated in the second internal space to the third internal space under a predetermined diffusion resistance; wherein the third internal space is provided with a third electro-chemical pump and a fourth electro-chemical pump on the third diffusion rate controlling passage, the third electro-chemical pump is so constructed that when the oxygen partial pressure of the atmosphere within the second internal space has a value which will not substantially reduce or decompose the object gas, the oxygen partial pressure is controlled to a further lower value which does not bring about any significant influence to the measurement of an amount of an object gas component, whereas the fourth electro-chemical pump is provided to reduce or decompose the object gas component introduced from the second internal space and to draw out an amount of oxygen generated at this moment; wherein the air introducing duct is provided in a manner such that the outside pump electrodes of the first and second electrochemical pumps are isolated so that these electrodes are not directly exposed to the object gas and that this duct can serve as oxygen sources when oxygen is introduced into the first internal space; the gas analyzer. further comprising: an operating section for operating the electro-chemical pumps provided in the first to third internal spaces of the gas sensor; a calculating section for performing a predetermined calculation on pumping currents flowing into the electro-chemical pumps so as to obtain a concentration value of the object gas component; a displaying/outputting section for displaying a value calculated in the calculating section or for outputting the value as an electric output; and a heater operating section for heating the gas sensor to a predetermined temperature; wherein plural known gas components are used as a standard gas, a pumping current with respect to the standard gas is calibrated as an analytical curve.

Further, according to the calibrating method of the present invention, it is preferred to use a standard gas containing at least $H_2O$ or $CO_2$ besides an object gas component as a known object gas component. Preferably, prior to measuring an analytic curve, the gas sensor is heated for a predetermined time to a temperature which is 50° C. higher than its working temperature, the gas sensor is then returned to its working temperature, thereby preparing and obtaining an analytical curve with the use of the standard gas. More preferably, prior to measuring an analytic curve, the gas sensor is separated from the operating section, an AC power source is connected to a point between each pair of electrodes in first to three treatment zones, an AC current having a frequency of 1 Hz or more is then caused to flow thereto, subsequently the gas sensor is returned to its driven state, thereby preparing and obtaining an analytical curve with the use of the standard gas.

DESCRIPTION OF THE PREFERRED EMBODIMENTS

In the following, a gas analyzer formed according to the present invention will be described in more detail with reference to the accompanying drawings. However, at first, the description will be given to explain in detail a gas sensor which forms an essential part of the gas analyzer of the present invention.

Figure 1:
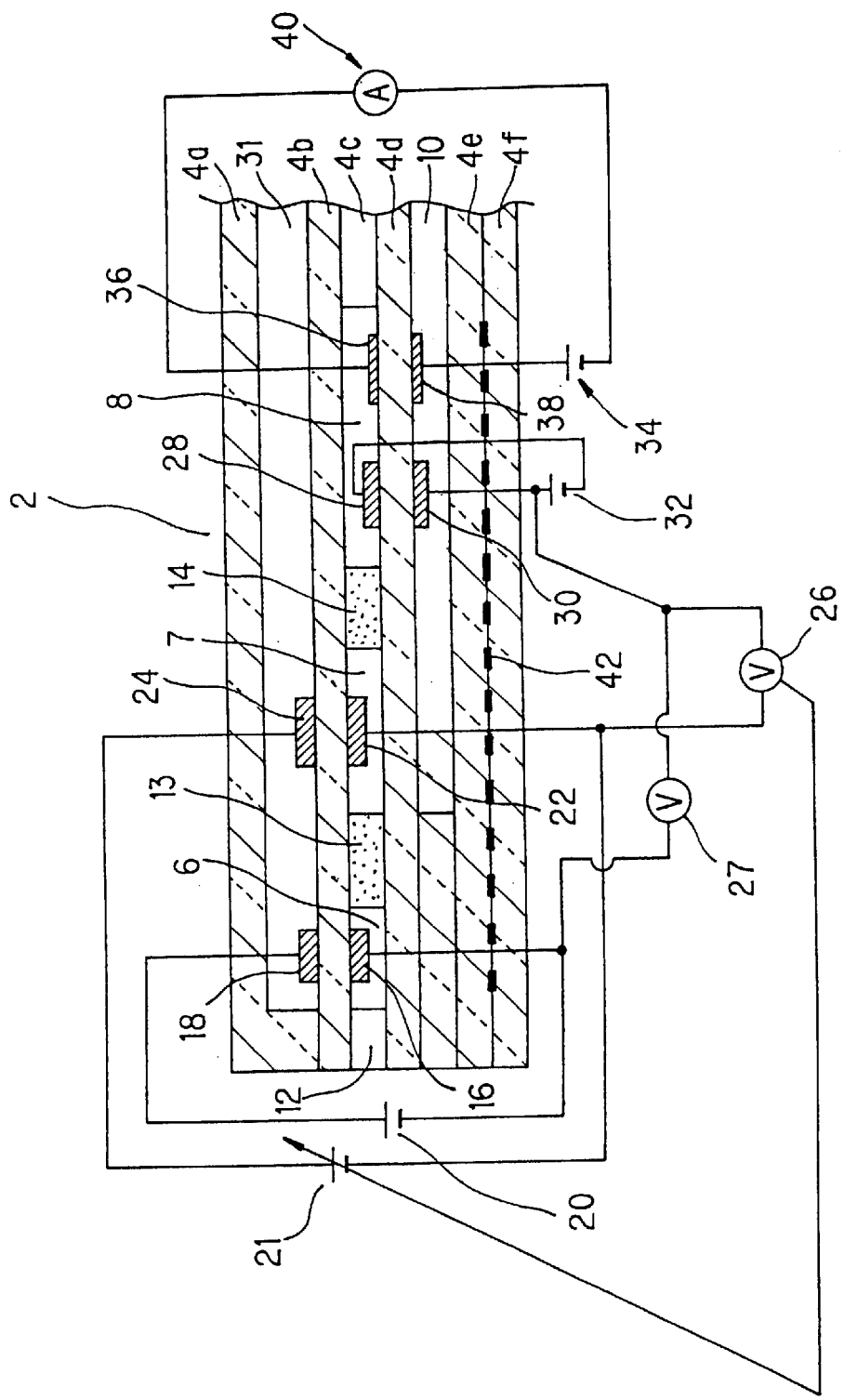
FIG. 1 is an enlarged explanatory view schematically indicating one embodiment of a gas sensor which forms an important part of a gas analyzer formed according to the present invention.

FIG. 1 is an enlarged view schematically indicating some important portions of the gas sensor which serves as essential part of the gas analyzer of the present invention. As shown in FIG. 1, a sensor device 2 is a plate-like member, which is made of an ion-conductive solid electrolytic material having a high tightness. For instance, the sensor device may be made of a known oxygen ion conductive solid electrolytic material such as zirconia porcelain. In fact, the sensor device 2 has an integrally formed structure, including a first internal space 6, a second internal space 7 and a third internal space 8, with each internal space having a rectangular parallelepiped configuration. In more detail, the first internal space 6 is located close to the front end of the sensor device while the third internal space 8 is located close to the rear end thereof, so that all the internal spaces are formed by dividing a large space from outside, thereby individually forming a first treatment zone, a second treatment zone, a third treatment zone and a fourth treatment zone. Although the first internal space 6, the second internal space 7 and the third internal space 8 are usually formed in the same plane, they may also be formed in different planes. Further, a standard gas introducing passage 10 serving as a standard gas existing space is formed in a manner such that it is in contact with most areas of the second internal space 7, by way of an oxygen ion conductive solid electrolytic material having a high air tightness. In more detail, the passage 10 is formed in parallel with both of the second internal space 7 and the third internal space 8, arranged in the longitudinal direction of the sensor device 2 extending towards the rear end thereof. Moreover, the standard gas introducing passage 10 has an opening located on the rear end of the sensor device 2, so that the passage 10 may be communicated with a zone including the surrounding atmosphere or a standard gas. Further, the standard gas introducing passage 10 is also an internal space defined by several solid electrolytic material layers, covered by the solid electrolytic material extending from the upper side thereof to the lower.

In addition, a first diffusion rate controlling passage 12 serving as a first rate controlling means is formed so that the first internal space 6 is communicated with an external space containing an object gas (which is to be measured). In fact, the first diffusion rate controlling passage 12 is provided near the front end of the sensor device 2 by forming small through holes or thin slits or porous passages in a solid electrolytic layer 4c. Alternatively, the first diffusion rate controlling passage 12 may be formed by filling the front end of the sensor device 2 with a porous material such as alumina. By way of the first rate controlling passage 12, an object gas, for example, a gas containing an object component (which is to be measured) such as $NO_x$ may be introduced into the first internal space 6 under a predetermined diffusion resistance. Similarly, a second diffusion rate controlling passage 13 is formed in the solid electrolytic layer 4c interposed between the first internal space 6 and the second internal space 7, whereas a third diffusion rate controlling passage 14 is formed in the solid electrolytic layer 4c interposed between the second internal space 7 and the third internal space 8. In the same manner, each of the second diffusion rate controlling passage 13 and the third diffusion rate controlling passage 14 may be formed by forming small through holes or thin slits or porous passages in a solid electrolytic layer 4c. Alternatively, they may be formed by filling the corresponding passage spaces with a porous material. Usually, the second diffusion rate controlling passage 13 and the third diffusion rate controlling passage 14 are both formed to exhibit a larger diffusion resistance than the diffusion resistance existing in the first diffusion rate controlling passage 12. In fact, the atmosphere within the first internal space 6 is introduced into the second internal space 7 through the second diffusion rate controlling passage 13 under a predetermined diffusion resistance, whereas the atmosphere within the second internal space 7 is introduced into the third internal space 8 through the third diffusion rate controlling passage 14 also under a predetermined diffusion resistance.

Furthermore, provided in an exposed portion of the first internal space 6 is a first internal pump electrode 16 consisting of a porous cermet electrode material having a rectangular parallelepiped configuration. In addition, a first external pump electrode 18 consisting of a porous cermet electrode material having a rectangular parallelepiped configuration is formed in contact with the outside surface of a solid electrolytic layer 4b, located in a position corresponding to the first internal pump electrode 16. In this way, a first electro-chemical pump cell is formed by virtue of the electrodes 16, 18 and the solid electrolytic layer 4b. Further, an electric current is supplied from an external variable power source 20 so that an electric current is caused to flow from the first internal pump electrode 16 to the first external pump electrode 18.

Therefore, an amount of oxygen may be obtained and introduced inwardly from the surrounding outside atmosphere containing a sufficient amount of oxygen enough for combustion of some combustible gases such as carbon oxide, hydrocarbons (hereinafter referred to as HC) and hydrogen contained in a gas which is existing within the first internal space 6 and is to be measured. For the above-mentioned introduction of oxygen, it is necessary to introduce oxygen from the outside pump electrode which is located at a place separate from the zone containing the object gas being measured.

In fact, the oxygen introduction may be effected by supplying a predetermined electric current or applying a predetermined voltage between the two electrodes 16 and 18. Of course, the oxygen concentration of a gas staying within the first internal space 6 may be monitored, so that the electric current or the voltage being applied between the two electrodes 16 and 18 may be controlled, thereby ensuring a desired amount of oxygen constantly existing within the first internal space 6.

In general, a porous cermet electrode is usually formed by a metal such as Pt and a ceramic such as $ZrO_2$. However, the first internal pump electrode 16 disposed within the first internal space 6 for being contacted by the object gas, is required to be made of a metal which has only a weakened reducibility when reducing the $NO_x$ component contained within the object gas or has not such a reducibility at all. For example, it is preferred to use a cermet material such as Pt—Au alloy and a ceramic material such as $ZrO_2$ to form the first internal pump electrode 16. In this way, during a process in which the oxygen is introduced into the first internal space 6, when the first external pump electrode 18 and a second external pump electrode 24 (which will be described later) are exposed to the object gas, the object component NOx will react with combustible gases and thus disappear if an air ratio X is less than 1, resulting in some severe errors in the measurement of the NOx component. For this reason, it is absolutely necessary that the first external pump electrode 18 and the second external pump electrode 24 be located in positions separate d from the object gas.

Accordingly, as shown in FIG. 1, it is preferred to dispose both of the first external pump electrode 18 and the second external pump electrode 24 away from the object gas, and to provide an air introducing duct 31 having an air introducing opening for introducing the surrounding outside atmosphere. Usually, the air introducing duct 31 is arranged to be parallel with both of the second internal space 7 and the third internal space 8, separate d by an oxygen ion conductive solid electrolytic material having a high air tightness.

In more detail, the air introducing duct 31 is formed in a manner such that it is arranged in the longitudinal direction of the sensor device 2 extending towards the rear end thereof, getting in contact with most areas of the second internal space 7. Preferably, the duct is also in contact with at least a part of the first internal space 6. Therefore, the first external pump electrode 18 is also located within the air introducing duct 31 consisting of the solid electrolytic layer 4a and the solid electrolytic layer 4b, in a manner shown in FIG. 1. However, if necessary, the first external pump electrode 18 can also be used as the second external pump electrode 24. Further, in order to introduce a sufficient amount of oxygen into the first internal space 6, it is necessary that the air introducing duct 31 should have a cross section having an area of at least 1 $mm^2$, with said cross section being perpendicular to the longitudinal direction of the sensor device 2.

Figure 6:
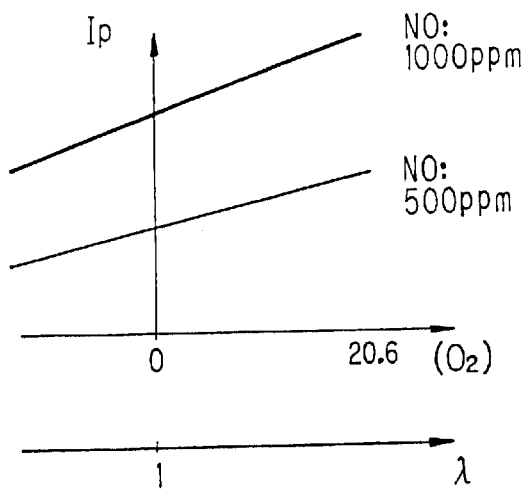
FIG. 6 is a graph showing an operating state of a gas sensor formed according to the present invention, indicating a relationship between an oxygen concentration and an electric current Ip4 obtained in a fourth electro-chemical cell provided in a third internal space when $NO_x$ and oxygen are coexisting therein.
Figure 8:
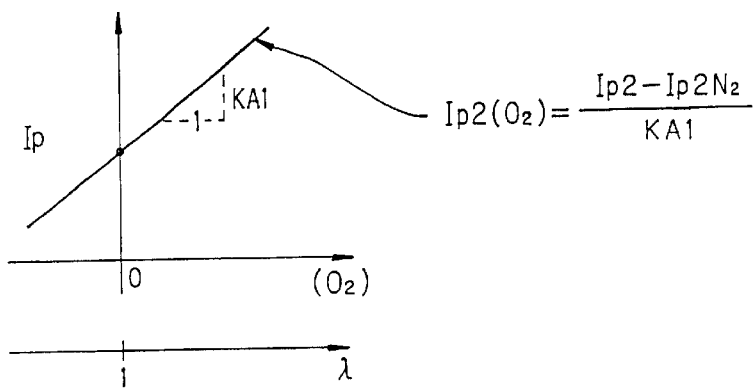
FIG. 8 is a graph showing an example of an operation of a gas sensor formed according to the present invention, indicating a relationship between an oxygen concentration and an electric current Ip2, the later of which is obtained in a second electro-chemical cell provided in a second internal space.

Furthermore, provided in an exposed portion of the second internal space 7 is a second internal pump electrode 22 consisting of a porous cermet electrode material which is just the same as the first internal pump electrode 16. In addition, the second external pump electrode 24 consisting of a porous cermet electrode material which is just the same as the first external pump electrode 18 is formed in contact with the outside surface of the solid electrolytic layer 4b, i.e., on the same outside surface where the first external pump electrode 18 is formed. Furthermore, a third external pump electrode and a fourth external pump electrode are provided in some exposed portions of the standard gas introducing passage 10. In this way, a second electro-chemical cell serving as an oxygen partial pressure detecting means is formed by virtue of the electrode 22, an electrode 30 or an electrode 38, further by virtue of the solid electrolytic layer 4d. Thus, in accordance with an oxygen concentration difference between an internal atmosphere within the second internal space 7 and the standard gas introducing passage 10 (surrounding outside atmosphere), an oxygen partial pressure of the atmosphere within the second internal space 7 may be detected by using a potentiometer 26, thereby detecting an electro motive force generated between the electrode 22 and the electrode 30 or the electrode 38. Then, in accordance with the value of the oxygen partial pressure of the atmosphere within the second internal space 7 (which has already been detected by the potentiometer 26), the voltage of the variable electric power source 21 may be controlled. Therefore, the pumping action of the second electro-chemical pump cell may be controlled in a manner such that the oxygen partial pressure of the atmosphere within the second internal space 7 will arrive at a value which is so low that the object gas component can not be reduced or decomposed and which is low enough for controlling an oxygen partial pressure in the third internal space 8. In this way, with the use of the present invention it has become possible to avoid a measurement deflection which will otherwise be caused under a condition where an oxygen concentration is high, thereby solving the problem pointed out in JP-A-9-113484. However, as shown in FIG. 6, with regard to the gas sensor formed according to the present invention, it is allowed to obtain a linear relationship between an oxygen concentration and an electric current Ip4 obtained in a fourth electro-chemical cell provided in the third internal space, with the relationship being true not only under a condition where the air ratio $\lambda$ is at least 1, but also under another condition where the air ratio $\lambda$ is less than 1. In fact, such a relationship can also be shown in FIG. 8, indicating that the straight line has almost the same gradient under two kinds of conditions of $\lambda<1$ and $\lambda \geq 1$, corresponding to an oxygen concentration in the second internal space. As a result, the following equation is obtained which is represented as:

$$NO_x \text{ Concentration} = (Ip4 - Ip4N_2)/(KA4 + \gamma x\, O_2)$$

wherein Ip4 represents an electric current output of the fourth treatment zone, $Ip4N_2$ represents an electric current value calibrated when $N_2$ is supplied to the fourth treatment zone, KA4 represents an electric current sensitivity coefficient of NO, which coefficient is the gradient of the straight line indicating a relationship between NO concentration and the electric current output Ip4 of the fourth treatment zone, $\gamma$ represents an oxygen concentration correcting coefficient obtained by dividing an increased amount of Ip4 (with respect to an increased oxygen concentration when $NO_x$ is existing) with a product obtained by multiplying $NO_x$ concentration with the oxygen concentration. On the other hand, as shown in FIG. 8, another linear relationship may be obtained between the oxygen concentration and the electric current Ip2 obtained in a fourth electro-chemical cell provided in the third internal space. As a result, the following equation is obtained which is represented as:

$$\text{Oxygen Concentration} = (Ip2 - Ip2N_2)/KA2$$

wherein Ip2 represents an electric current output of the second treatment zone, $Ip2N_2$ represents an electric current value calibrated when $N_2$ is supplied to the second treatment zone, KA2 represents an electric current sensitivity coefficient of $O_2$, which coefficient is the gradient of the straight line indicating a relationship between the oxygen concentration and the electric current output Ip2 of the second treatment zone.

With the use of the above two equations, it is possible to correctly calculate $NO_x$ concentration and thus easily facilitate the $NO_x$ measurement without having to pay attention to the variation of the oxygen concentration.

The third internal space 8 has the third treatment zone provided with a third electro-chemical cell consisting of the third internal pump electrode 28 and the third external pump electrode 30. The third internal space also has the fourth treatment zone provided with a fourth electro-chemical cell consisting of the fourth internal pump electrode 36 and the fourth external pump electrode 38. In fact, the third and fourth electro-chemical cells are separated from each other at a certain distance. In detail, the third internal pump electrode 28 is made of the same porous cermet electrode material as used in forming the first internal pump electrode 16. Further, the third external pump electrode 30 is made of the same porous cermet electrode material as that used for forming the first external pump electrode 18, which is provided in an exposed portion of the standard gas introducing passage 10 formed by the solid electrolytic layer 4d, with the electrode 30 being located in a position corresponding to the electrode 28. In this way, the third electro-chemical pump cell is thus formed by the internal pump electrode 28, the external pump electrode 30 and the solid electrolytic layer 4d. Then, an external DC power source 32 is used to apply a predetermined voltage between the two electrodes 28 and 30 of the third electro-chemical pump cell, so as to enable an electric current to flow from the third external pump electrode 30 to the third internal pump electrode 28. As a result, the oxygen partial pressure of the object gas introduced into the sensor device by way of the third diffusion rate controlling passage may be constantly controlled at a low value. Therefore, in the vicinity of the inlet of the third internal space 7, an object gas component such as $NO_x$ will be under a condition where $NO_x$ will not be reduced or decomposed, thus it is sure to avoid any unfavorable influence on the measurement of an object gas component.

Moreover, the fourth internal pump electrode 36 having a rectangular shape is provided within the fourth treatment zone formed in the third internal space 8, in a manner such that it is separate d from the third electro-chemical cell at a predetermined distance. In detail, the fourth internal pump electrode 36 may be formed by a porous cermet electrode material consisting of a ceramic such as $ZrO_2$ and a metal such as Ph and Pt (each capable of reducing $NO_x$ which is an object gas component). Further, the fourth internal pump electrode functions as a catalyst for reducing the object component $NO_x$ existing in the atmosphere within the third internal space 8 by constituting it in a such manner as mentioned above. At the same time, a DC power source 34 is used to apply a predetermined voltage between the internal pump electrode 36 and the fourth external pump electrode 38 disposed in the standard gas introducing passage 10, so that the oxygen contained in the atmosphere of the fourth treatment zone within the third internal space 8 may be introduced into the standard gas introducing passage 10. In this way, the fourth electro-chemical pump cell is thus formed by virtue of the fourth internal pump electrode 36, the fourth external pump electrode 38 and the solid electrolytic layer 4d. Then, the pump current flowing by virtue of a pumping action of the fourth electro-chemical pump cell may be detected by an ampere meter 40. In fact, the DC power source 34 can produce a constant voltage which is high enough to provide a limiting current. Under a condition where the $NO_x$ is flowing at a rate limited by the third diffusion rate controlling passage 14, the above voltage is applied with respect to the pumping action for pumping the oxygen generated when the $NO_x$ is decomposed by virtue of the fourth electro-chemical pump cell.

Further, a heater 42 is buried within the sensor device 2, in a manner such that it is interposed between the solid electrolytic layer 4e and the solid electrolytic layer 4f, and that it can produce a heat once an electric power is supplied from the outside of the sensor device. Moreover, although not shown in the drawing, each of the upper and lower surfaces of the heater 42 is covered up by a thin layer made of a ceramic such as alumina, thereby forming an insulation between the heater and the solid electrolytic layers. Furthermore, as shown in FIG. 1, the heater 42 is formed in an area extending from the first internal space 6 to the third internal space 8. In this way, the first, second and third internal spaces 6, 7 and 8 may be heated to a predetermined temperature, so that the first, second, third and fourth electro-chemical pump cells can be heated to and maintained at a predetermined temperature.

In use, the sensor device 2 having the above-described structure is usually set in a manner such that its front end is positioned in a space containing an object gas which is to be measured. In this manner, the object gas to be measured is caused to pass through the first diffusion rate controlling passage 12 provided within the sensor device 2, and is further introduced into the first internal space 6 under a predetermined diffusion resistance. Then, the object gas introduced in the first internal space receives an oxygen pumping action produced by applying an electric current or an electric voltage between the two electrodes 16 and 18 which together form the first electro-chemical pump cell, so that the oxygen concentration of the object gas may be controlled to contain a sufficient amount of oxygen to effect a desired combustion of the combustible gases contained within the object gas. Here, the sufficient amount of oxygen capable of effecting the desired combustion is meant to represent an oxygen concentration which can constantly maintain an oxygen amount contained in the atmosphere of the first internal space at an adequate level, even if the combustible gas components theoretically contained in the object gas have been completely burned. Usually, if an adjustment is performed so that the oxygen concentration of the atmosphere within the first internal space can be kept at 1% or more, such an adjustment may be considered to be sufficient.

In practice, if it is desired to set the oxygen concentration of the atmosphere in the first internal space 6 at a predetermined value, a necessary operation is only to supply a predetermined electric current or to apply a predetermined voltage between the two electrodes 16 and 18 of the first electro-chemical pump cell, thereby effecting the oxygen introduction at a desired manner. Further, it is also possible to use another method based on Nernst's equation, in which a potentiometer 26 or a potentiometer 27 is used to measure an electro motive force between the electrode 16 (or the electrode 22) and the electrode 30 (or the electrode 36), and a control operation is performed to control a voltage (a variable voltage 20) being applied between the two electrodes 16 and 18 of the first electro-chemical pump cell. Namely, a necessary operation is only to control an output voltage of the first electro-chemical pump cell, in a manner such that the output voltage becomes equal to an electro motive force generated due to a difference between a predetermined oxygen concentration in the first internal space 6 and a reference oxygen concentration. Here, the first diffusion rate controlling passage 12 is provided such that when a voltage is applied to the first electro-chemical pump cell, a diffusion flow rate for the oxygen of the object gas to flow into a measurement space (the first internal space 6) may be converged, so as to control the electric current following into the first electro-chemical pump cell. In this way, by virtue of the oxygen pumping action of the first electro-chemical pump cell, an amount of oxygen is introduced into the first treatment zone from the air introducing duct 31, so that the oxygen concentration of the atmosphere within the first treatment zone may be controlled to ensure a sufficient amount of the oxygen capable of effecting a sufficient combustion of the combustible gas components contained in the object gas.

However, with regard to the first internal space 6, even if the space is heated by an object gas introduced from the outside and even if it is under a condition where it is heated by the heater 42, further, even if an amount of oxygen existing in the atmosphere within the first internal space 6 has been completely used up in the combustion of the combustible gas components (in a manner such that $NO_x$ existing in the atmosphere is not reduced due to the first internal pump electrode 16 and the second internal pump electrode 22), the first internal space 6 will still be in a state having a sufficient oxygen partial pressure, e.g., in a state having an oxygen partial pressure which does not cause a reaction $NO \rightarrow 1/2\ N_2 + 1/2\ O_2$. The reason for this may be explained as follow. Namely, if $NO_x$ existing in the atmosphere within the first internal space 6 is reduced, it is impossible to correctly measure $NO_x$ in the third internal space at a later step. This means that the first internal space 6 should have a proper electrode and a proper oxygen partial pressure, both of which are such that $NO_x$ will not be reduced even if there is a component (metal component of the internal pump electrode 16) relating to the reduction of the $NO_x$. In addition, the second internal space is provided with the second electro-chemical cell. The potentiometer 26 is used to measure an electro motive force generated between the electrode 22 and the electrode 30 or the electrode 38, thereby detecting the oxygen partial pressure in the atmosphere within the second internal space 7, based on an oxygen concentration difference between the atmosphere within the second internal space 7 and the atmosphere passing through the standard gas introducing passage 10. Then, in accordance with the value of the oxygen partial pressure, which has been detected by the potentiometer 26, of the atmosphere within the second internal space 7, the output of the variable electric power source 21 is controlled and the pumping action of the second electro-chemical pump cell is also controlled in a manner such that the oxygen partial pressure of the atmosphere within the second internal space 7, under a condition where the object gas component to be measured will not be decomposed, will drop to its sufficiently low value so as to effect a desired control of the oxygen partial pressure in the third treatment zone within the third internal space 8.

Subsequently, the object gas whose oxygen partial pressure has been controlled in the second internal space 7, is caused to flow through the third diffusion controlling passage 14 and is then introduced into the third internal space 8 under a predetermined diffusion resistance. Further, the third diffusion control passage 14 within the third internal space 8 is provided with the third electro-chemical pump cell (4d, 28, 30) in order that the oxygen partial pressure of the atmosphere within the space may be constantly maintained at a certain low value. By virtue of the pumping action of the pump cell and by detecting the oxygen partial pressure of the third internal space 8, even if the oxygen partial pressure of the atmosphere introduced from the second internal space 7 will change corresponding to the oxygen concentration of the gas treated in the first internal space 6, since the oxygen partial pressure of the atmosphere within the third internal space 8 may be constantly controlled at a relatively low value, it is still possible for the oxygen partial pressure to be kept at a relatively low value which does not substantially bring about any unfavourable influence to the result of measurement of $NO_x$.

However, the interior of the third internal space 8 is made just the same as that of the first internal space 6. Namely, under a condition where the third internal space is being heated by an external gas to be measured or being heated by the heater 42, the third internal space may be controlled by the third internal pump electrode 28 so that it will be in a state having an oxygen partial pressure which does not cause reduction of $NO_x$ existing in the atmosphere within the third internal space. Accordingly, the third internal pump electrode 28 is required to be made of the same material as used in forming the first internal pump electrode 16 and the measurement electrode 22, i.e., using an electrode material having no reducibility on the object gas or at most has only a reduced reducibility.

In this way, the measured gas is introduced into the third internal space 8 and is further treated by the third electro-chemical pump cell in the third treatment zone. Then, the measured gas is allowed to receive an oxygen pumping action in the fourth treatment zone by applying a predetermined voltage between the fourth internal pump electrode 36 and the fourth external pump electrode 38 which together form the fourth electro-chemical pump cell, with the voltage application being along a direction in which oxygen is introduced from the third internal space 8 to the standard gas introducing passage 10. In this way, the fourth treatment zone which is an internal space located opposite to the third diffusion rate controlling passage 14 of the third internal space 8, may be controlled at such a state that $NO_x$ will not be reduced. This is particularly true for the three-phase interface of the fourth internal pump electrode 36, and further for the surrounding areas of the internal pump electrode 36 capable of reducing the oxygen concentration and serving as a catalyst for reducing $NO_x$. At this moment, the value of an electric current flowing into the fourth electro-chemical pump cell is proportional to an oxygen concentration of an atmosphere being introduced into the fourth treatment zone in the fourth internal space 8, i.e., proportional to a sum of two oxygen concentrations, with one being an oxygen concentration of an atmosphere within the third treatment zone in the third internal space 8, and the other being an oxygen concentration generated by virtue of both the fourth internal pump electrode 36 and reduction of $NO_x$. However, since an oxygen concentration of an atmosphere within the third internal space may be controlled by the third electro-chemical pump cell, the value of an electric current flowing into the fourth electro-chemical pump cell will be proportional to the concentration of $NO_x$. In this way, $NO_x$ concentration will be corresponding to $NO_x$ diffusion amount limited by the third diffusion rate controlling passage 14, thereby making it possible to measure the concentration of $NO_x$.

Figure 2:
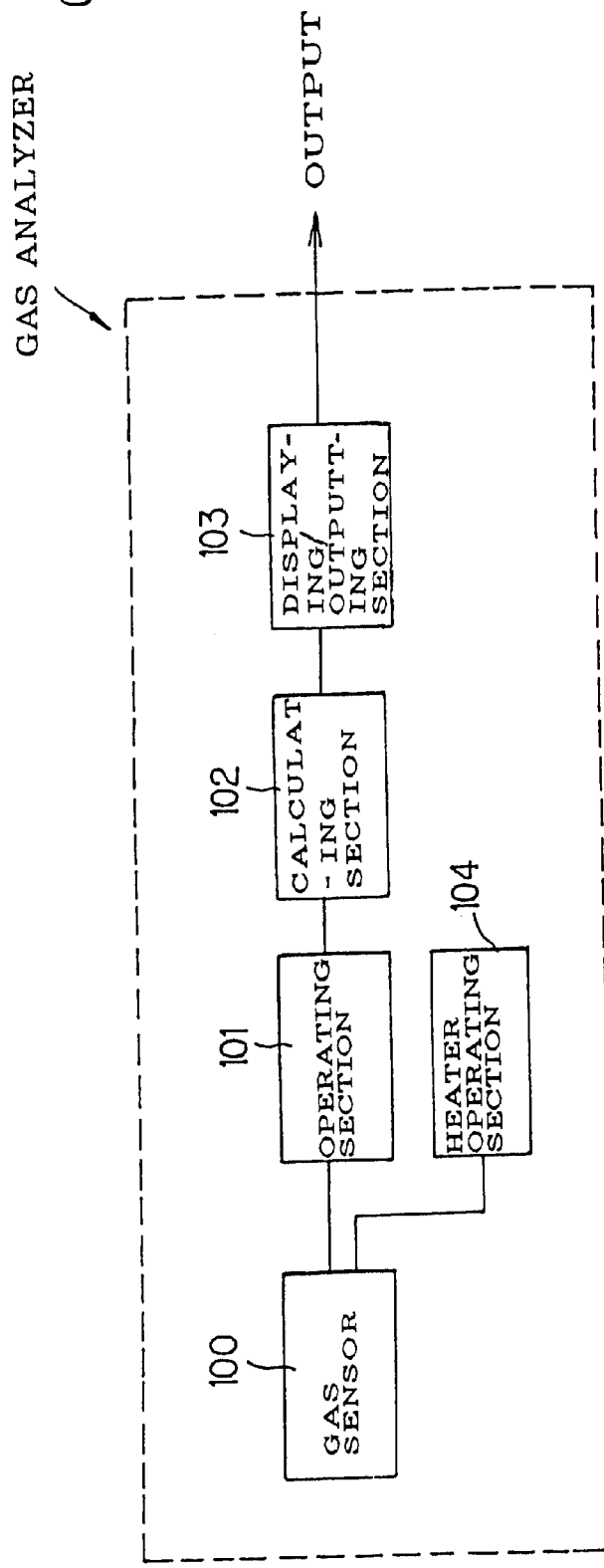
FIG. 2 is a block diagram indicating one example of a gas analyzer formed according to the present invention.

Next, the gas analyzer of the present invention containing the above gas sensor will be described with reference to the accompanying drawings. Here, FIG. 2 is a block diagram indicating one example of a gas analyzer formed according to the present invention. As shown in the drawing, the inventive gas analyzer comprises a gas sensor 100, an operating section 101 for pumping oxygen to the gas sensor 100, a calculating section 102 for calculating values of certain gas components by processing several pumping currents flowing to electro-chemical pump cells of the gas sensor 100, a displaying/outputting section 103 for displaying values calculated by the calculating section 102 or outputting the values as electric signals, a heater operating section 104 for heating the gas sensor 100 to a predetermined temperature. Further, the gas sensor 100 can serve as an independent unit which may be separated from the gas analyzer. Namely, the gas analyzer is comprised of the operating section 101, the calculating section 102, the displaying/outputting section 103 and the heater operating section 104. Therefore, the gas sensor 100 may be positioned on the outside of the gas analyzer and is connected therewith through a cable.

Here, the calculating section 102 has a function of calculating a value of a gas component by processing a pumping current flowing to the fourth electro-chemical pump cell of the gas sensor. In addition, the calculating section 102 is further capable of introducing thereinto a pumping current (Ip1) of the first treatment zone, a pumping current (Ip2) of the second treatment zone, a pumping current (Ip3) of the third treatment zone. By processing the pumping currents in the calculating section 102, it is possible to calculate and produce an oxygen concentration, an air/fuel ratio A/F or an air ratio λ of the object gas. Actually, these calculations are based on the following fact indicating that (A×Ip1+B×Ip2+C×Ip3+D×Ip4) is proportional to a total oxygen amount contained in the object gas. Here, A, B, C and D are all constants, Ip4 represents a pumping current following into the fourth electro-chemical pump cell, i.e., a pumping current in the fourth treatment zone.

Further, according to the present invention, the value of oxygen concentration or the value of the air/fuel ratio A/F or the value of the air ratio λ of the object gas may be used to correct $NO_x$ concentration of the gas. At this time, as the oxygen concentration, the air/fuel ratio A/F and the air ratio λ, all useful for correcting the $NO_x$ concentration, it is preferred to use the values calculated in accordance with (Ip1+Ip2+Ip3+Ip4). More conveniently, it is also allowed to use the values calculated in accordance with (Ip2) or (Ip2+Ip3).

Figure 7:
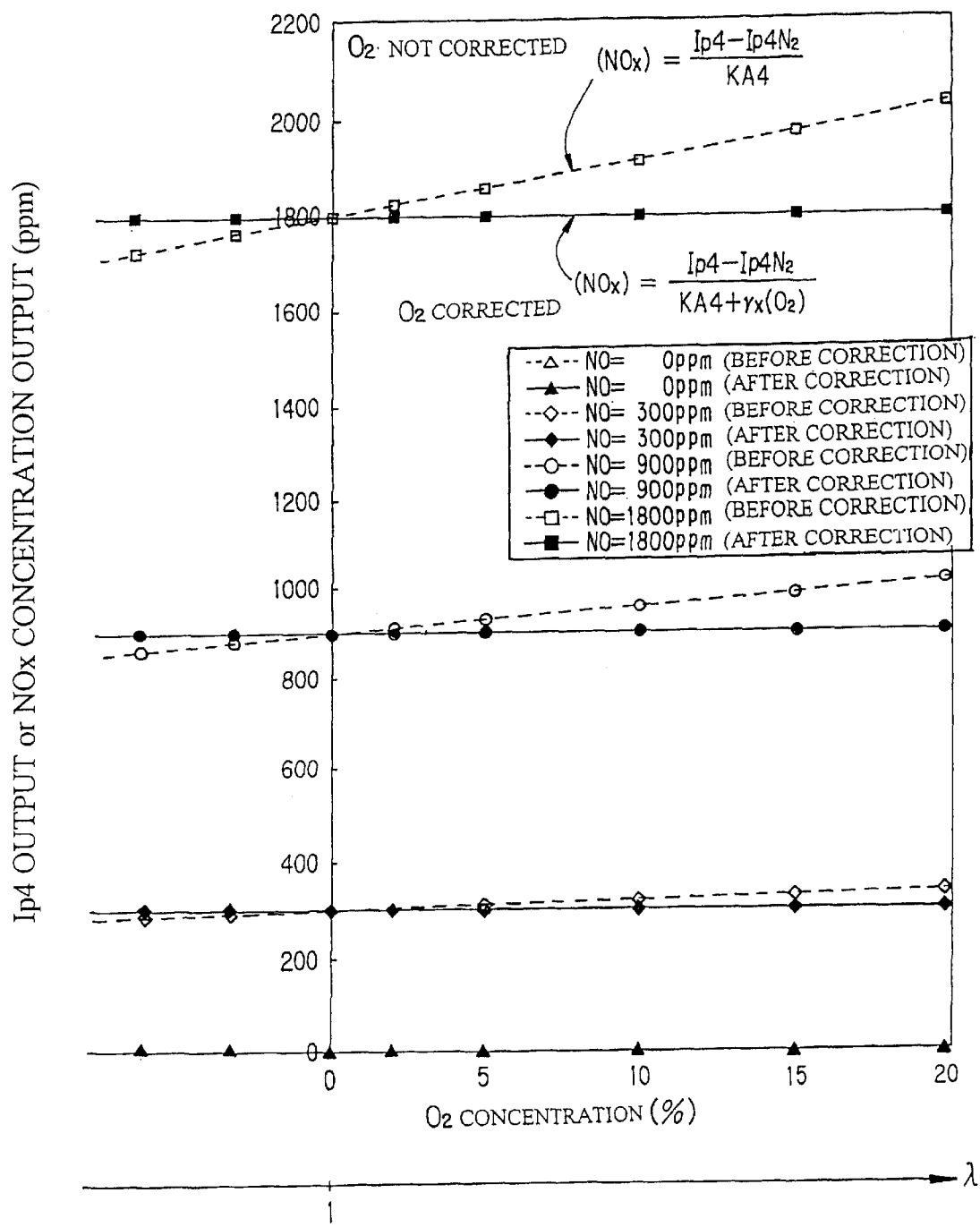
FIG. 7 is a graph showing an operating state of a gas sensor formed according to the present invention, indicating an oxygen concentration and $NO_x$ concentration, the later of which is obtained as an output of a pump current (Ip4) when a gas containing $NO_x$ at a concentration of 300 to 1800 ppm is introduced into a first diffusion rate controlling passage. In this graph, various darkened marks are used to represent data where a concentration correction has been carried out using an output of Ip2, while various bright marks are used to represent data where a concentration correction has not been conducted using the output of Ip2.
Figure 9:
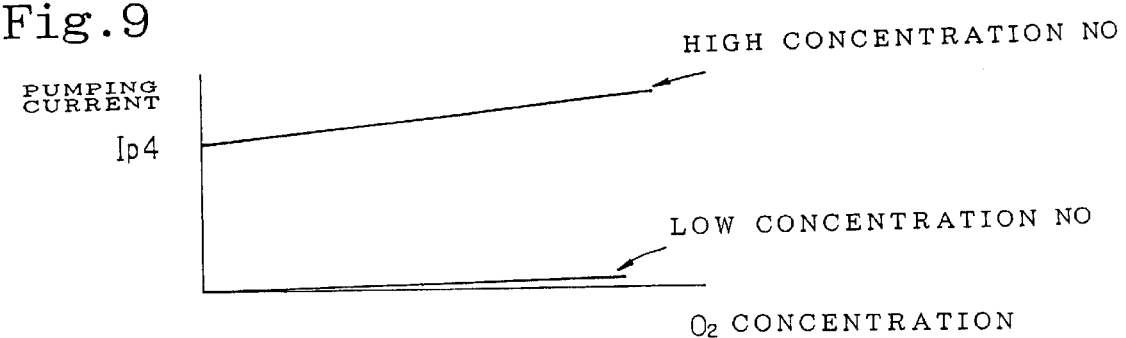
FIG. 9 is a graph indicating a relationship between an electric current Ip4 and an oxygen concentration of an object gas, at a time $NO_x$ and oxygen are coexisting therein.

In the following, description will be given to explain a detailed example about how to use an oxygen concentration to correct a measured value of $NO_x$ concentration. When the object gas to be measured contains both $NO_x$ and oxygen, as shown in FIG. 9, the pumping current (Ip4) in the fourth treatment zone will vary depending on the oxygen concentration of the gas. Namely, during a process in which the oxygen concentration of the gas changes, a higher concentration of the $NO_x$ coexisting with the oxygen will cause a larger change in the pumping current (Ip4). Accordingly, in the present invention, since the output signal of the $NO_x$ sensor will vary depending upon the oxygen concentration, the air/fuel ratio A/F or the air ratio λ, an output signal represented by the pumping current (Ip4) can be corrected by making use of the second pumping current (Ip2), thereby making it possible to perform a correct detection of $NO_x$ component. This relationship may be made more understandable with reference to FIG. 7. As shown in FIG. 7, when the gas sensor of the present invention is used and a gas containing $NO_x$ at a concentration of 300 to 1800 ppm is introduced into the first diffusion rate controlling passage, it is allowed to obtain a graph in which $NO_x$ concentration is indicated corresponding to the oxygen concentration and the output of the pumping current (Ip4). In FIG. 7, various darkened marks are used to represent data corrected by using the second pumping current Ip2, whereas various bright marks are used to represent data not corrected by using the second pumping current Ip2. As may be clearly understood from the graph, when oxygen concentration is high, $NO_x$ concentration will also be detected to be high, corresponding to a high oxygen concentration (if the correction as described in the above is not performed). FIG. 9 is a graph indicating an example in which the above correction has been made to avoid a problem that $NO_x$ concentration depends upon an oxygen concentration. However, it is also possible to provide some other examples indicating that if the horizontal axis of a graph is used to represent the air/fuel ratio A/F and the air ratio λ, it is sure to correct the value of $NO_x$ concentration which varies depending on a reductive gas, a natural gas or an oxidative gas.

Figure 3:
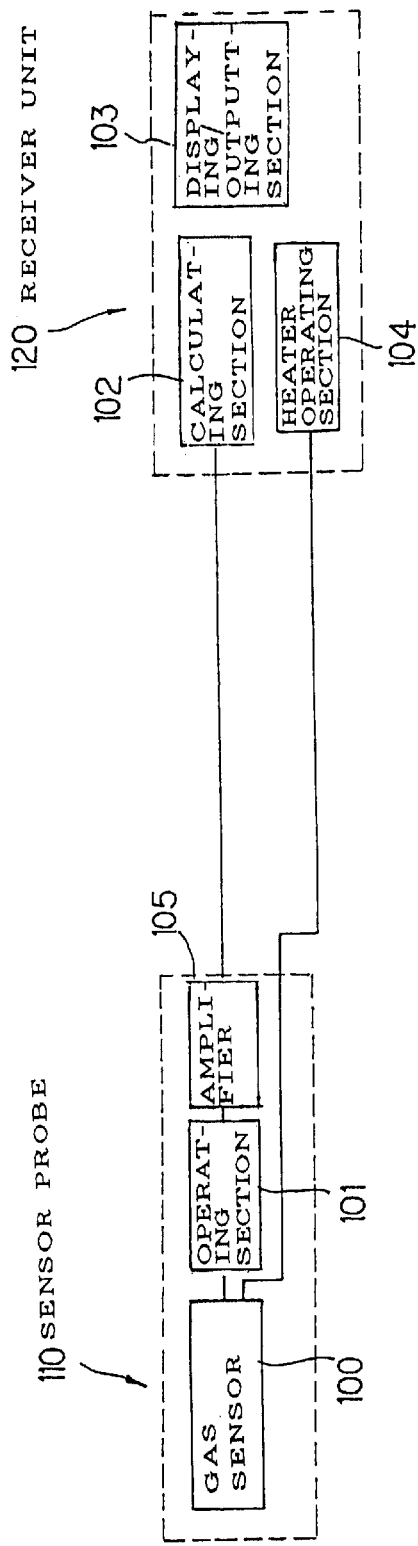
FIG. 3 is a block diagram indicating another example of a gas analyzer formed according to the present invention.

FIG. 3 is a block diagram indicating another example of a gas analyzer formed according to the present invention. In fact, the gas analyzer shown in FIG. 3 is also formed in accordance with a structure where a gas sensor is separated from a receiver unit. In detail, the gas analyzer has a sensor probe 110 integrally including a gas sensor 100, an operating section 101 for pumping oxygen to the gas sensor 100, an amplifier 105 for amplifying a pumping current obtained in the operating section 101. Further, the gas sensor has a receiver unit 120 located in a position which is separated from the sensor probe 110. The receiver unit 120 includes a calculating section 102, a displaying/outputting section 103, a heater operating section 104.

Figure 4:
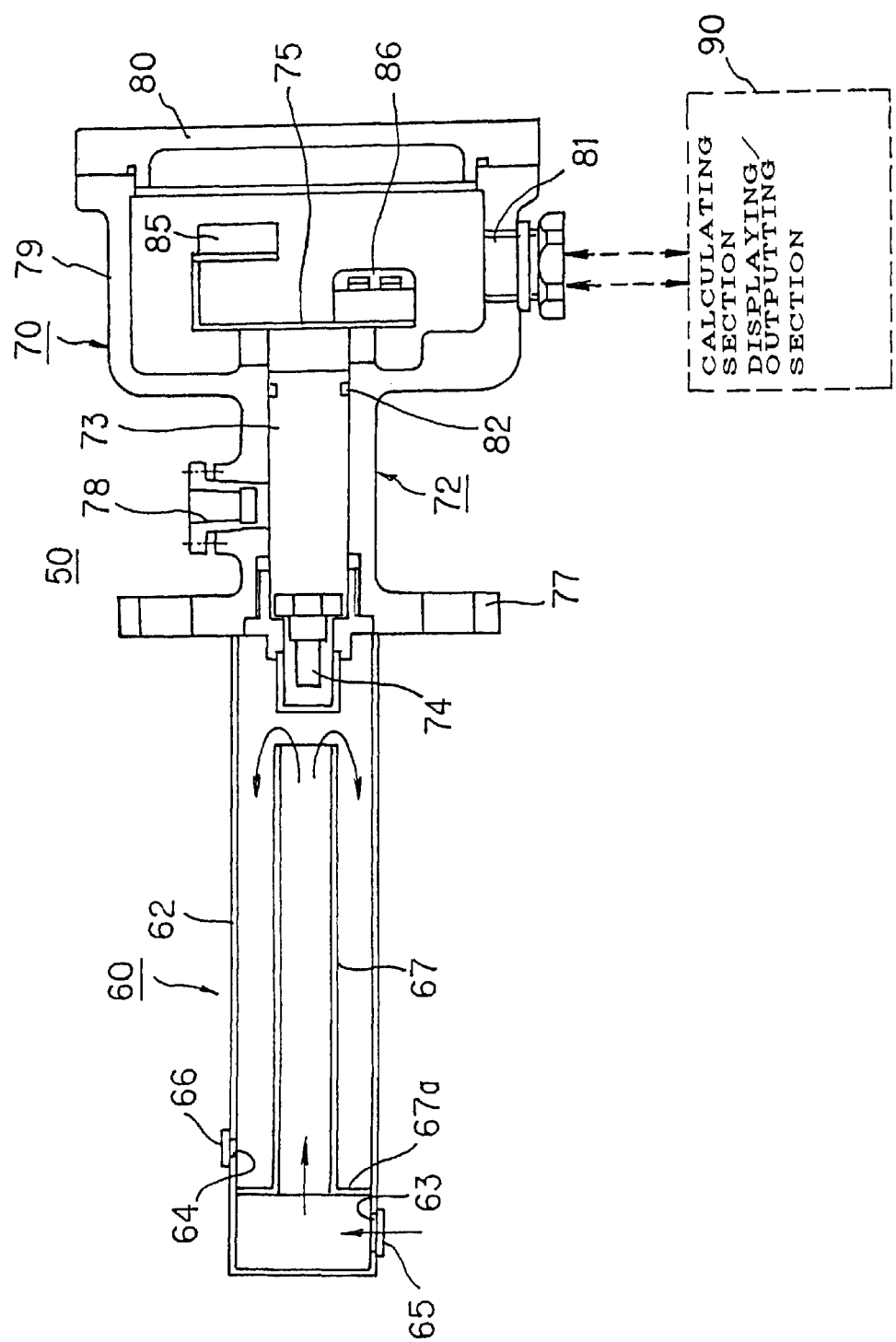
FIG. 4 is an explanatory view schematically indicating a detailed structure of the gas analyzer shown by a block diagram in FIG. 3.
Figure 5:
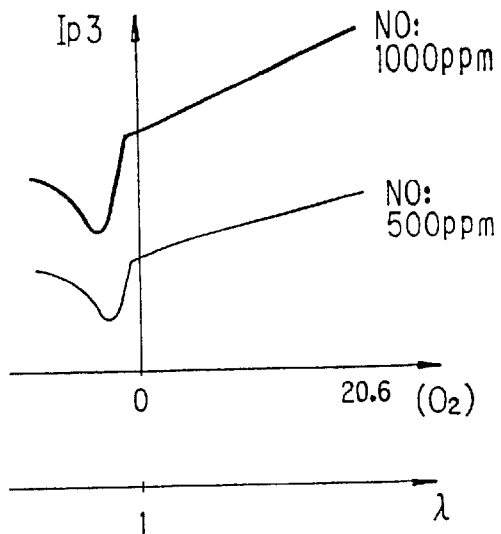
FIG. 5 is a graph showing an operating state of a conventional gas sensor, indicating a relationship between an oxygen concentration and an electric current Ip3 obtained in a third electro-chemical cell provided in a second internal space when $NO_x$ and oxygen are coexisting therein.

FIG. 4 is an explanatory view schematically indicating in more detail the gas analyzer shown by a block diagram in FIG. 3.

Referring to FIG. 4, a gas analyzer 50 comprises a gas introducing section 60 and a $NO_x$ detecting section 70. The gas introducing section 60 has a cylindrical probe 62. Close to the front end of the cylindrical probe 62 are formed a gas inlet 63 and a gas outlet 64 which are spaced apart from each other by a certain distance. In fact, the gas inlet 63 and the gas outlet 64 are provided with gratings 65 and 66 which are thus also separated from each other. Further, the probe 62 contains an inner tube 67 which is formed with a flange portion 67a at one end thereof and is located in a position coaxial with the probe 62. With the use of the structure shown in FIG. 4, an object gas to be measured is introduced into the probe through the gas inlet 63. The introduced gas is then caused to flow through the inner tube 67, turning over the inner end of the tube so as to flow into an annular space formed between the inner tube 67 and internal surface of the probe 62. Finally, the gas is discharged out of the probe 62 by way of the gas outlet 64.

The $NO_x$ detecting section 70 includes a main body 72 and a $NO_x$ sensing unit 73 received into the main body. The $NO_x$ sensing unit 73 has a plate-like $NO_x$ sensor 74 one end of which is exposed and the other end of which is connected with a terminal mounting base 75 through a screw means, so that the $NO_x$ sensor 74 is allowed to be electrically connected to the outside of the section. Further, around the outer periphery surface of the detecting section main body 72 is provided a flange member 77 which is used to connect together the gas introducing section 60 and the $NO_x$ detecting section 70.

In addition, a calibration gas inlet 78 is provided in the middle portion of the detecting section main body 72 in order that a calibration gas can be supplied to the $NO_x$ sensor 74. Moreover, on one end of the detecting section main body 72, which is opposite to an end where the $NO_x$ sensor 74 is located, there are provided a cover 80 and a flange case 79 enclosing the terminal mounting base 75. Further, on one side of the flange case 79 there is provided a wiring hole 81 for leading electrodes or the like (wiring in the operating section as will be described in detail later in this specification) extending from the terminal mounting base 75 out of the detecting section main body 72. In addition, an O-ring 82 is provided on the internal surface of the detecting section main body 72 so as to prevent the gas from leaking towards the terminal mounting base 75. Moreover, a terminal screw 86 is attached to the terminal mounting base 75, in a manner such that the terminal mounting base 75 and the $NO_x$ sensing unit 73 may be fixed in predetermined positions within the $NO_x$ detecting section 70.

The terminal mounting base 75 is equipped with an operating section 85 containing an amplifier. In fact, the operating section 85 is electrically connected to a receiver unit 90 containing a calculating section as well as a displaying/outputting section, thereby effecting the desired pumping of the $NO_x$ sensor 74 and the predetermined calculation, as well as the signal displaying or outputting. Thus, by disposing the operating section in the vicinity of the gas sensor, the pumping current of the operating section can be amplified by the amplifier and then introduced to the calculating section, thereby reducing an electric noise.

Further, with regard to the gas analyzer formed according to the present invention, it is preferred that a pumping current (Ip4) be measured which varies corresponding to the concentrations of several known gas components, and that an analytical curve be prepared, thereby calibrating the gas analyzer. Namely, within the calculating section of the gas analyzer, the data of the pumping current (Ip4) which varies corresponding to the concentrations of several known gas components is accumulated. Then, by making use of the accumulated data, the pumping currents (Ip4) for the gas components (to be measured) are converted into the concentrations of the gas components, followed by calibration of the concentrations.

Figure 10:
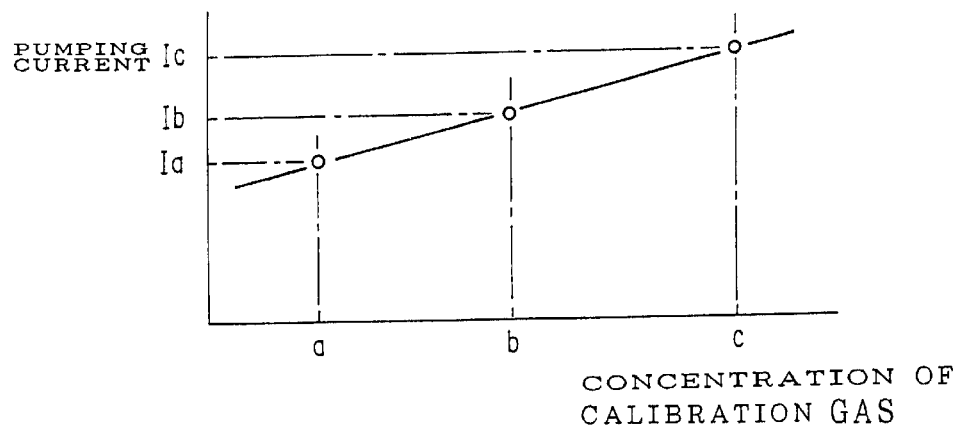
FIG. 10 is a graph indicating an example of an analytical curve.

For example, as shown in FIG. 10, various calibration gases (standard gases) having different concentrations a, b, c are used to perform the measurement, thereby obtaining pumping currents (Ia, Ib, Ic) to be measured at that moment. Then, an analytic curve is prepared which is one-order linear curve or multi-order curve. With the use of the calculating section, it is possible to automatically prepare the analytical curve. In addition, it is particularly preferred to measure an oxygen dependency or an air ratio dependency mentioned earlier in this specification, thereby calibrating the analytical curve.

Figure 11:
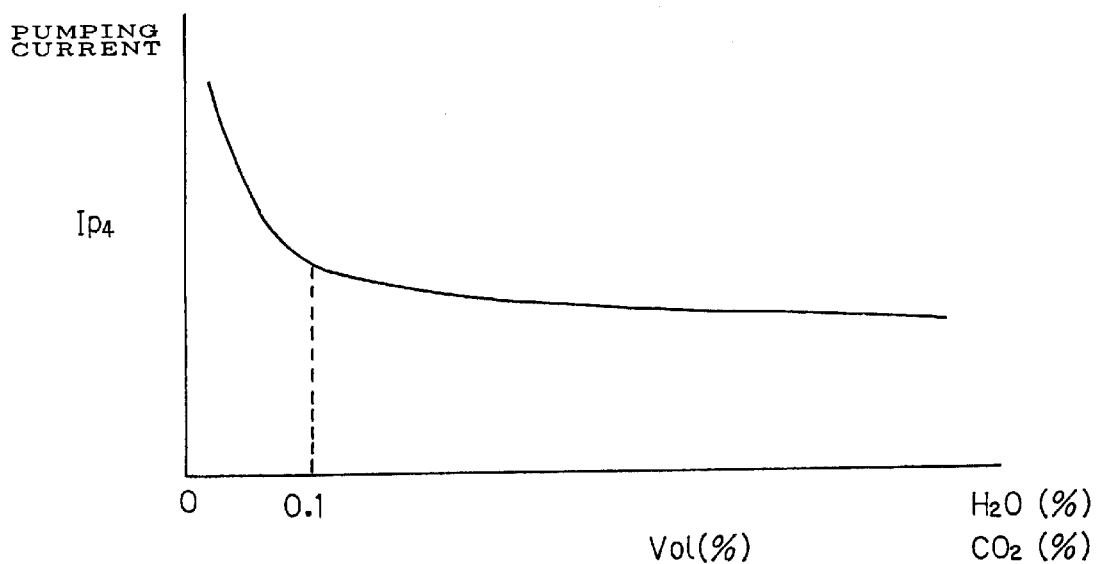
FIG. 11 is a graph indicating a relationship between a pumping current Ip4 and an amount of $H_2O$ and $CO_2$ contained in a calibration gas.

When using the gas analyzer of the present invention, it is preferred to employ the above analytic curve to carry out the calibration. However, as the known gas components (calibration gases) to be measured, apart from the known gas components mentioned in the above, it is also allowed to use a gas containing at least one of gases $H_2O$ and $CO_2$. As may be understood from FIG. 11, if the calibration gases do not contain $H_2O$ and $CO_2$, an electro motive force generated by the solid electrolytic substance will become low, so that the pumping current (Ip4) will be increased. Accordingly, an unstable condition will sometimes occur, making it difficult to ensure a desired reliability for the concentrations of gas components to be measured. On the other hand, if the calibration gases contain at least one of the gases $H_2O$ and $CO_2$, the pumping current (Ip4) will become stable. The reason for this phenomenon may be explained as follows. Namely, the surface state of the electrodes formed by the solid electrolytic material will become stabilized by $H_2O$ and $CO_2$. However, an adding amount for adding $H_2O$ and $CO_2$ is preferred to be 0.1 vol % or more, more preferably 1 vol % or more, which is an amount including one or both of them.

Further, with the gas analyzer of the present invention, it has been found that during a predetermined period before or after the use of the gas analyzer, CO, OH or some poisoning substances will be excessively absorbed on the electrodes which are formed by the solid electrolytic material and which form an electro-chemical pumping cell, hence lowering the detecting precision of the gas analyzer. Here, it is preferred that before the measurement of the analytical curve, the poisoning substances be desorbed from the solid electrolytic electrodes, so as to calibrate the electrodes to have them kept at a correct normal state. There have been known several methods for effecting such a desorption, which can generally be classified into two sorts. One sort is to heat the sensor to a high temperature (a high temperature method) and the other sort is to forcefully cause an electric current to flow through the sensor (a forced energizing method). The most preferably used method is that the gas sensor equipped with the electro-chemical pump cell is heated during a predetermined time to a temperature which is 50 degrees higher than the operation temperature of the sensor. Then, the temperature of the sensor is returned to its operation temperature, thereby preparing the analytical curve with the use of the calibration gas (using the high temperature method). Here, a time period for keeping the sensor at a high temperature is set to be about 10 minutes, a sufficient time period for the above treatment. On the other hand, in the forced energizing method, the sensor is separated from the operating section, an AC current is connected to a point between each pair of electrodes in the first to fourth treatment zones. For example, after an AC current having a frequency of 1 Hz or more has been caused to flow through the sensor for a predetermined time period, the sensor is then returned to its driven state, thereby making it possible to prepare the analytical curve with the use of the calibration gas. Here, a time period for flowing the AC current is set to be about 10 minutes, a sufficient time period for the above treatment.

Although the present invention has been described in detail in this specification, it should be understood that this invention can also receive various changes, modifications and improvements in accordance with some general knowledge of an ordinary skill in the art. Further, such kind of changes, modifications and improvements should be considered to be within the scope of the present invention, provided that they do not depart from the spirit described in the present specification.

As may be understood from the above description, with the use of the gas analyzer and the gas analyzer calibrating method of the present invention, it has become possible to obtain a pumping current and an electro motive force, both of which are very stable with respect to the concentration of an object gas component (to be measured) such as $NO_x$. Thus, a concentration of a gas component such as $NO_x$, which in a prior art could be detected only in a lean area where an air ratio λ is 1 or more, can be measured in a stoichometric area where the air ratio λ is in the vicinity of 1, as well as in a rich area where the air ratio λ is less than 1. In this way, it has become possible to correctly measure the concentration of a gas component.

What is claimed is:

1. A gas analyzer comprising:
   a gas sensor which includes a first diffusion rate controlling passage, a first internal space communicated with the first diffusion rate controlling passage, a second diffusion rate controlling passage, a second internal space communicated with the second diffusion rate controlling passage, a third diffusion rate controlling passage, a third internal space communicated with the third diffusion rate controlling passage, and an air introducing duct;

wherein the first diffusion rate controlling passage is a passage provided for introducing an object gas containing an object component including a sort of combined oxygen from an external gas existing space to the first internal space under a predetermined diffusion resistance;

wherein the first internal space is provided for effecting the combustion of some combustible gases, and is provided with a first electro-chemical pump for adjusting an oxygen partial pressure within the first internal space, so that the internal space constantly contains a sufficient amount of oxygen capable of effecting the combustion of the combustible gases contained in the object gas which has been introduced into the internal space through the first diffusion rate controlling passage;

wherein the second diffusion rate controlling passage is a passage provided for introducing the object gas treated in the first internal space to the second internal space under a predetermined diffusion resistance;

wherein the second internal space is provided with a second electro-chemical pump which is so constructed that when an amount of oxygen is drawn from the second internal space atmosphere consisting of the object gas introduced into the second internal space through the second diffusion rate controlling passage, the oxygen partial pressure is decreased to a sufficiently low value which does not reduce or decompose the object gas and which is low enough for controlling the oxygen partial pressure in a third treatment zone;

wherein the third diffusion rate controlling passage is a passage provided for introducing the object gas treated in the second internal space to the third internal space under a predetermined diffusion resistance;

wherein the third internal space is provided with a third electro-chemical pump next to the third diffusion rate controlling passage and a fourth electro-chemical pump next to the third electro-chemical pump, the third electro-chemical pump is so constructed that when the oxygen partial pressure of the atmosphere within the second internal space has a value which will not substantially reduce or decompose the object gas, the oxygen partial pressure is controlled to a further lower value which does not bring about any significant influence to the measurement of an amount of an object gas component, whereas the fourth electro-chemical pump is provided to reduce or decompose the object gas component introduced from the second internal space and to draw out an amount of oxygen generated at this moment;

wherein the air introducing duct is provided in a manner such that the outside pump electrodes of the first and second electro-chemical pumps are isolated so that these electrodes are not directly exposed to the object gas and that this duct can serve as oxygen sources when oxygen is introduced into the first internal space;

the gas analyzer further comprising:

an operating section for operating the electro-chemical pumps provided in the first to third internal spaces of the gas sensor;

a calculating section for performing a predetermined calculation on pumping currents flowing into the electro-chemical pumps so as to obtain a concentration value of the object gas component;

a displaying/outputting section for displaying a value calculated in the calculating section or for outputting the value as an electric output; and a heater operating section for heating the gas sensor to a predetermined temperature.

2. A gas analyzer according to claim 1, wherein among the electrodes of the electro-chemical pumps, all the outside pump electrodes not existing in the first to third internal spaces are isolated so that these electrodes are not directly exposed to the object gas.

3. A gas analyzer according to claim 1, wherein the object gas component is $NO_x$.

4. A gas analyzer according to claim 3, wherein each calculated value of $NO_x$ concentration which has a correlation with the oxygen partial pressure is calibrated in accordance with an output of the second electro-chemical pump.

5. A gas analyzer according to claim 1, wherein at least the operating section is integrally formed with the gas sensor.

6. A gas analyzer calibrating method for use with a gas analyzer which comprises:

a gas sensor which includes a first diffusion rate controlling passage, a first internal space communicated with the first diffusion rate controlling passage, a second diffusion rate controlling passage, a second internal space communicated with the second diffusion rate controlling passage, a third diffusion rate controlling passage, a third internal space communicated with the third diffusion rate controlling passage, and an air introducing duct;

wherein the first diffusion rate controlling passage is a passage provided for introducing an object gas containing an object component including a sort of combined oxygen from an external gas existing space to the first internal space under a predetermined diffusion resistance;

wherein the first internal space is provided for effecting the combustion of some combustible gases, and is provided with a first electro-chemical pump for adjusting an oxygen partial pressure within the first internal space, so that the internal space constantly contains a sufficient amount of oxygen capable of effecting the combustion of the combustible gases contained in the object gas which has been introduced into the internal space through the first diffusion rate controlling passage;

wherein the second diffusion rate controlling passage is a passage provided for introducing the object gas treated in the first internal space to the second internal space under a predetermined diffusion resistance;

wherein the second internal space is provided with a second electro-chemical pump which is so constructed that when an amount of oxygen is drawn from the second internal space atmosphere consisting of the object gas introduced into the second internal space through the second diffusion rate controlling passage, the oxygen partial pressure is decreased to a sufficiently low value which does not reduce or decompose the object gas and which is low enough for controlling the oxygen partial pressure in a third treatment zone;

wherein the third diffusion rate controlling passage is a passage provided for introducing the object gas treated in the second internal space to the third internal space under a predetermined diffusion resistance;

wherein the third internal space is provided with a third electro-chemical pump next to the third diffusion rate controlling passage and a fourth electro-chemical pump next to the third electro-chemical pump, the third electro-chemical pump is so constructed that when the oxygen partial pressure of the atmosphere within the second internal space has a value which will not substantially reduce or decompose the object gas, the oxygen partial pressure is controlled to a further lower value which does not bring about any significant influence to the measurement of an amount of an object gas component, whereas the fourth electro-chemical pump is provided to reduce or decompose the object gas component introduced from the second internal space and to draw out an amount of oxygen generated at this moment;

wherein the air introducing duct is provided in a manner such that the outside pump electrodes of the first and second electro-chemical pumps are isolated so that these electrodes are not directly exposed to the object gas and that this duct can serve as oxygen sources when oxygen is introduced into the first internal space;

the gas analyzer further comprising:

an operating section for operating the electro-chemical pumps provided in the first to third internal spaces of the gas sensor;

a calculating section for performing a predetermined calculation on pumping currents flowing into the electro-chemical pumps so as to obtain a concentration value of the object gas component;

a displaying/outputting section for displaying a value calculated in the calculating section or for outputting the value as an electric output; and a heater operating section for heating the gas sensor to a predetermined temperature;

wherein plural known gas components are used as a standard gas, a pumping current with respect to the standard gas is calibrated as an analytical curve.

7. A gas analyzer calibrating method according to claim 6, wherein a standard gas containing at least $H_2O$ or $CO_2$ besides an object gas component is used as a known object gas component.

8. A gas analyzer calibrating method according to claim 6, wherein prior to measuring an analytic curve, the gas sensor is heated for a predetermined time to a temperature which is 50° C. higher than its working temperature, the gas sensor is then returned to its working temperature, thereby preparing and obtaining an analytical curve with the use of the standard gas.

9. A gas analyzer calibrating method according to claim 6, wherein prior to measuring an analytic curve, the gas sensor is separated from the operating section, an AC power source is connected to a point between each pair of electrodes in first to three treatment zones, an AC current having a frequency of 1 Hz or more is then caused to flow thereto, subsequently the gas sensor is returned to its driven state, thereby preparing and obtaining an analytical curve with the use of the standard gas.

* * * * *